(12) United States Patent
Brocia

(10) Patent No.: US 10,195,163 B2
(45) Date of Patent: Feb. 5, 2019

(54) ENERGY DRINKS AND OTHER NUTRITIONAL AIDS DERIVED FROM AGAVE-BASED SPIRITS

(71) Applicant: ROAR HOLDING LLC, New York, NY (US)

(72) Inventor: Robert W. Brocia, Bronxville, NY (US)

(73) Assignee: ROAR HOLDING LLC, New York, NY (US)

( * ) Notice: Subject to any disclaimer, the term of this patent is extended or adjusted under 35 U.S.C. 154(b) by 524 days.

(21) Appl. No.: 14/856,438

(22) Filed: Sep. 16, 2015

(65) Prior Publication Data

US 2016/0074343 A1    Mar. 17, 2016

Related U.S. Application Data

(60) Provisional application No. 62/071,179, filed on Sep. 16, 2014, provisional application No. 62/231,592, filed on Jul. 10, 2015.

(51) Int. Cl.

| *A61K 31/138* | (2006.01) |
|---|---|
| *A61K 31/137* | (2006.01) |
| *C12Q 1/32* | (2006.01) |
| *C12Q 1/26* | (2006.01) |
| *C12G 3/08* | (2006.01) |
| *G01N 33/14* | (2006.01) |
| *A23L 2/38* | (2006.01) |
| *A23L 33/105* | (2016.01) |
| *G01N 33/569* | (2006.01) |
| *A61K 36/00* | (2006.01) |

(52) U.S. Cl.
CPC ............. *A61K 31/138* (2013.01); *A23L 2/38* (2013.01); *A23L 33/105* (2016.08); *A61K 31/137* (2013.01); *C12G 3/085* (2013.01); *C12Q 1/26* (2013.01); *C12Q 1/32* (2013.01); *G01N 33/146* (2013.01); *G01N 33/56972* (2013.01); *A61K 36/00* (2013.01); *G01N 2333/904* (2013.01); *G01N 2333/90638* (2013.01); *G01N 2500/02* (2013.01)

(58) Field of Classification Search
None
See application file for complete search history.

(56) References Cited

U.S. PATENT DOCUMENTS

| 4,612,196 A | 9/1986 | Goldstein et al. |
|---|---|---|
| 8,409,834 B2 | 4/2013 | Burlew et al. |
| 2010/0178411 A1 | 7/2010 | Mayer |
| 2014/0106014 A1 | 4/2014 | Giuliano et al. |

FOREIGN PATENT DOCUMENTS

| EP | 0 531 155 | 3/1993 |
|---|---|---|
| WO | WO-2011/022682 | 2/2011 |
| WO | WO-2014/015417 | 1/2014 |

OTHER PUBLICATIONS

International Search Report and Written Opinion for PCT/US15/50509, dated Dec. 8, 2015, 8 pages.
Vazquez-Landaverde and Rodriguez-Olvera, "Tequila Processing and Flavor," in: Flavor Chemistry of Wine and Other Alcoholic Beverages, Qian and Shellhammer (eds.), American Chemical Society (2012) Ch. 15, pp. 237-276.
Supplementary European Search Report for EP 15843033.0, dated Jan. 30, 2018, 12 pages.

*Primary Examiner* — Susan Hoffman
(74) *Attorney, Agent, or Firm* — Morrison & Foerster LLP

(57) ABSTRACT

Compositions containing monoamine oxidase inhibitors prepared by removal of alcohol from agave-derived beverages are disclosed.

11 Claims, 5 Drawing Sheets

ENERGY DRINKS AND OTHER NUTRITIONAL AIDS DERIVED FROM AGAVE-BASED SPIRITS

RELATED APPLICATION

This application claims benefit of U.S. provisional application Ser. No. 62/071,179 filed 16 Sep. 2014 and of U.S. provisional application Ser. No. 62/231,592 filed 10 Jul. 2015 the contents of these applications are incorporated herein by reference in their entirety.

TECHNICAL FIELD

The invention relates to non-alcoholic versions of agave-based spirits, in particular various tequilas, that are useful in treating a variety of conditions by virtue of monoamine oxidase (MAO) inhibitors contained in these drinks.

BACKGROUND ART

There is an extensive literature related to preparation of distilled spirits from agave. For example, a detailed description of the preparation of tequila from agave cactus is provided in *Tequila Processing and Flavor*, Pedro A. Vazquez-Landaverde and Miriam G. Rodriguez-Olvera, Centro de Investigación en Ciencia Aplicada y Tecnologfa Avanzada del Instituto Politécnico Nacional Unidad Querretaro, Cerro Blanco 141 Colinas del Cimatario, Queretaro, Qro., Mexico 76090; 2012 American Chemical Society; on the World Wide Web at //pubs.acs.org, Publication Date (Web): Jul. 16, 2012| doi: 10.1021/bk-2012-1104.ch015 In Flavor Chemistry of Wine and Other Alcoholic Beverages; Qian, M., et al.; ACS Symposium Series; American Chemical Society: Washington, D C, 2012, the disclosure of which is incorporated herein by reference for its description of treatment of the agave starting materials, fermentation, distillation and aging. Briefly, stems of the agave cactus are heated to hydrolyze complex sugars and shredded and crushed to release a syrup. The syrup is then diluted with water to provide a suitable dilution for inoculation with yeast. After fermenting, the fermentation culture is distilled to obtain a distillate. The distillate is sold as various brands of tequila of which there are many. The distillate, however, may be aged before packaging and selling.

The specific description set forth in the above-referenced source is as follows:

The mature agave stripped of leaves (referred to as the "pifia") is cut in halves, quarters, or more, in order to make it easier for oven (48 h) or autoclave (12 h) baking at 106-116° C. This thermal treatment has the objective of hydrolyzing complex sugars like inulin and starch, to obtain glucose and fructose for an easier fermentation. Sugars result mainly in ethanol formation, many other compounds arise from the fermentation of this substrate. Resulting from the thermal treatment of the pifias, compounds are formed, mainly Maillard-related such as furans, pyrans, aldehydes, nitrogen and sulfur compounds. The most abundant Maillard compounds are methyl-2-furoate, 2,3-dihydroxy-3,5-dihydro-6-methyl-4(H)-pyran-4-one and 5-hydroxymethylfurfural. Pyrazines are also an important group of chemical compounds derived from Maillard reactions. Most abundant pyrazines found are 2,5-dimethylpyrazine and trimethylpyrazine.

Other thermally-related breakdown products arise during the baking step. Free fatty acids of short- and long-carbon chain have been found in baked pifias probably due to hydrolysis of acylglycerols, β-cyclocitral and β-damascenone are likely degradation products of carotenoids, while 4-methyl-5-(2-hydroxyethyl)-thiazole is a breakdown product of the amino acid thiamine Phenols like p-cresol and 4-ethyl phenol are a breakdown product of phenolic acids.

Once the pifias are baked, they are taken to a shredding mill and a crusher where they release all the syrup containing high concentration of sugars and the majority of the compounds. The resulting agave mash is often washed off in order to improve sugar extraction.

There is no doubt that fermentation is the most important and complicated stage of agave processing. 100% agave or mixto syrups are diluted with water to reach 12-14° BRIX (80-100 g/L of sugar). Fermentation takes place in thermostatized tanks at 30° C., although some processes are carried out at room temperature, which could be variable depending on the season of the year. Fermentation depends entirely of the metabolism of yeasts and in less extent of lactic and acetic acid bacteria. Many strains of yeasts have been found in agave musts, being *Saccharomyces cerevisiae* and *Kloeckera africana* the most important ones. Yeasts metabolize carbohydrates, amino acids, fatty acids and other organic compounds, transforming them into ethanol, glycerol, carbon dioxide, and in a less extent into aldehydes, ketones, higher alcohols, organic acids and esters, which are called "fermentation by-products" or "congeners." Higher alcohols, also called "fusel alcohols" because of their malty and burnt flavor, are formed by degradation of amino acids via keto acids (2-oxo acids). The most important ones are 1-propanol, 2-methyl-1-propanol, 2-methyl-butanol, 3-methyl-butanol, and 2-phenylethanol, the later having a rose-like aroma. Synthesis of fatty acids inside the yeast cell forms mainly saturated straight-chain fatty acids with an even number of 4 to 18 carbon atoms, and the appearance of low levels of fatty acids with odd carbon numbers and unsaturations depends on the fermentation conditions. Fatty acids can combine with alcohols to form esters.

Fermentation proceeds for 18 to 24 hours at 30 to 35° C. A processing temperature of 35° C. produces more volatile compounds than 30° C. Also, it has been observed that supplementation with a nitrogen source changes compound formation by yeasts during fermentation, although the effect is different depending on the nitrogen source used. By adding a mixture of 20 amino acids, *Kloeckera africana* strain K1 is able to produce and tolerate higher ethanol concentrations, while the production of some esters, alcohols, acetaldehyde and α-terpineol is increased. When using *Saccharomyces cerevisiae* in a must supplemented with sodium sulfate and amino acids, the concentration of amyl alcohols and isobutanol decrease, while propanol an acetaldehyde increase.

Once the fermentation is over, and alcohol content reaches about 15% v/v, it is time for distillation. The fermented mash is heated in copper or stainless steel kettles at 78-80° C. so evaporation of alcohol is achieved. Vapors are condensed in cooled coils and a distillate is collected. First distillate reaches an alcohol concentration of ~25% v/v, and needs a second distillation also called rectification, in order to reach ~55% v/v of ethanol. The liquid is then adjusted with water to 38-40% v/v alcohol. Since the majority of compounds are volatile, they are evaporated along with ethanol during distillation. It is possible to separate different fractions of volatiles or "cuts" during distillation. The head cut contains highly volatile compounds like acetaldehyde and ethyl acetate, whereas the tail cut has higher boiling point chemicals such as ethyl esters of long-chained fatty acids. Since the both fractions are undesirable, they can be separated from the heart cut. Methanol is obtained in the tail, despite its low boiling point. Ethyl lactate, acetic acid and furfural are also distilled in the tail fraction. Isobutyl and isoamyl alcohols behave as head products, n-propyl alcohol is found in the heart, and phenethyl alcohol exhibits a tail product behavior.

Heat plays an important role on compound generation during distillation. Because of this it is possible that some breakdown reactions take place, and formation of aldehydes, ketones, furans, sulfur compounds, pyrazines, and phenols occur.

The rectified distillate adjusted with water to 40% ethanol content may be aged for two months to three years in oak casks. Aldehydes evaporate and/or form acetals. By aging in wooden casks, volatile compounds such as vanillin, guaiacol, eugenol, cresol and other phenolics migrate from the wood to the distillate, up-rounding the flavor. Ethyl esters are not only formed during fermentation, but also during aging. It has been reported that esters may be formed subsequently during the aging process by esterification of fatty acids with ethanol at high concentrations.

The foregoing description is as found in the above-referenced document. A wide variety and multiplicity of compounds that are components of agave extracts and/or spirits prepared from them have been identified; however, to applicant's knowledge, it has not been understood that the beverages commonly marketed as tequila or others derived from agave contain MAO inhibition activity. As it is known that MAO inhibitors can be used as mood elevators, anti-depressants and treatments for various other diseases, including Parkinson's disease, the non-alcoholic "energy drink" that is comprised of the alcohol-free components of these beverages is useful in these contexts.

DISCLOSURE OF THE INVENTION

As noted above, the invention takes advantage of the presence of MAO inhibitors in spirits prepared from agave extracts. The MAO inhibitors may be initially present in the extract or formed during fermentation or formed during distillation or aging and combinations of the above. In particular, applicant has shown that removing the alcohol from these commercially available spirits by applying a vacuum destroys at least some of the MAO inhibition activity. Therefore, the compositions of the present invention must be prepared from these spirits by processes that preserve these volatile components. These processes include reverse osmosis, spin columns and other methods that do not result in the loss of volatile compounds.

Accordingly, in one aspect, the invention is directed to a composition prepared by subjecting to reverse osmosis or other volatile component conserving process an agave derived alcoholic beverage. In one embodiment, the agave derived alcoholic beverage has been prepared by heating the stems of agave cactus to hydrolyze complex sugars; shredding and crushing the heated stems to release a syrup; diluting said syrup with water to a 12-14 BRIX level and inoculating with yeast; fermenting the inoculated diluted syrup to obtain a fermentation product; and distilling the fermentation product to obtain a distillate.

The invention is also directed to methods to treat conditions characterized by overactivity of MAO by administering to a subject in need of such treatment an effective amount of the composition of the invention. This is particularly relevant in the case of depression or Parkinson's disease.

In addition, the invention is directed to a method to assay for MAO inhibition activity in the presence of ethanol. Ethanol in significant amounts interferes with the assay. Accordingly, standard assays which do not account for the presence of alcohol will provide misleading results.

Thus, in another aspect, the invention is directed to a method to assay for MAO inhibitors in the presence of ethanol which method comprises adding to the assay nicotinamide adenine dinucleotide and alcohol dehydrogenase. In more detail the assay comprises adding to the sample to be analyzed a substrate-effective amount of kynuramine dihydrobromide, along with nicotinamide adenine dinucleotide and alcohol dehydrogenase; adding MAO A or MAO B; incubating at 37° C.; stopping the reaction with strong base and assessing the results with an excitation wavelength of 310 nm and an emission wavelength of 405 nm.

MODES OF CARRYING OUT THE INVENTION

Figure 1:
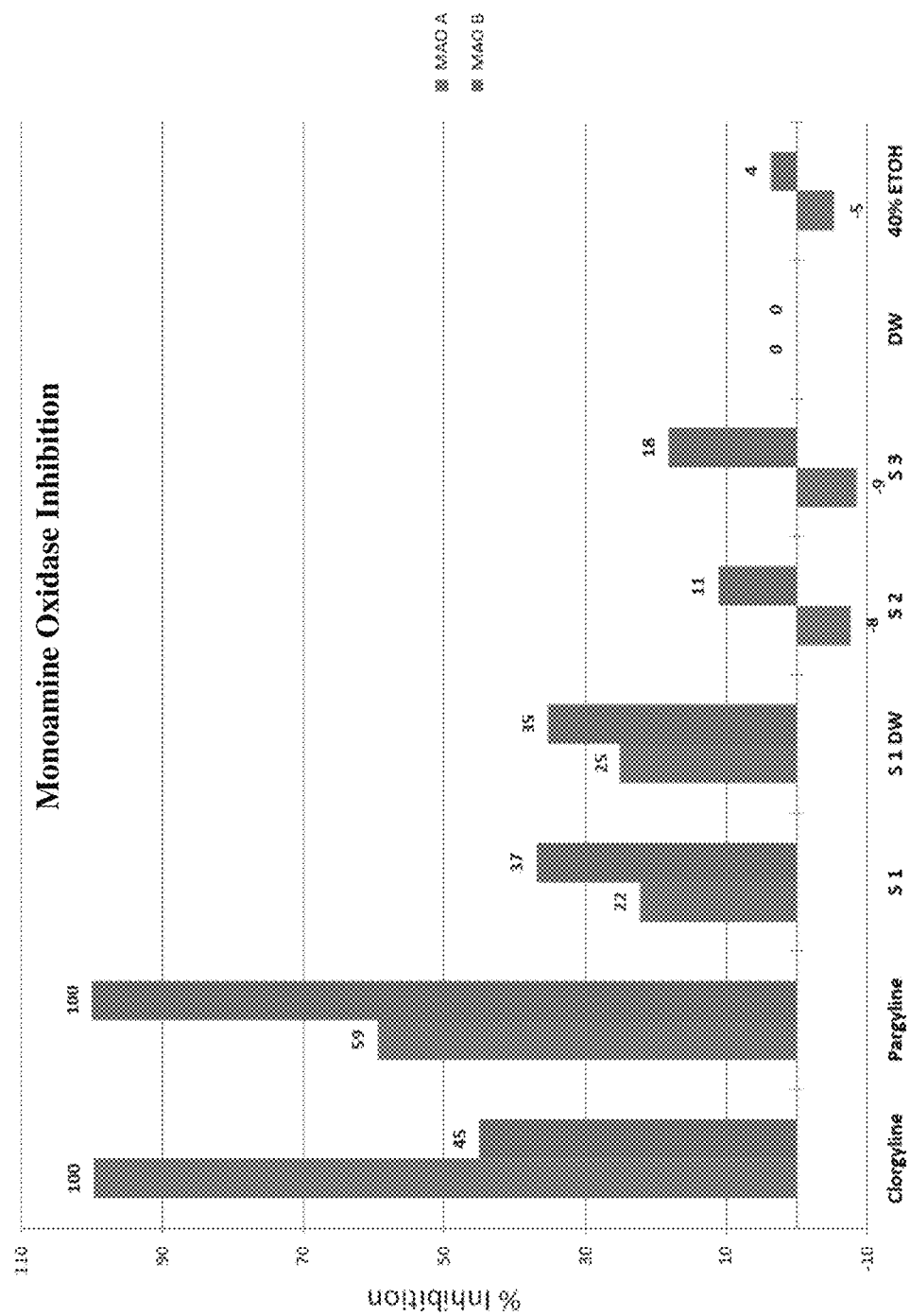
FIG. 1 shows the results of assessment of MAO inhibition activity in a tequila at various ages as assessed by a standard commercial assay kit.

The non-alcoholic forms of alcoholic beverages made from the agave plant extracts are the subject of the present invention. These alcoholic beverages include pulque, tequila, mezcal, sotol, Bacanora or other ferments made from agave-plant-derived-sugars. In the present invention the alcohol has been removed under conditions where other volatile compounds are retained.

These compositions have monoamine oxidase (MAO) inhibitory properties and are thus useful for use as mood elevators, antidepressants or treatment for certain diseases such as Parkinson's disease. The invention also relates to a method of grading and preparation or mixing different extracts to select a desired physiological stimulant or anti-depressant effect for use as an energy drink and/or mood elevator by assessing MAO activity in the presence of alcohol. In the grading/evaluation tool aspect of the invention, different agave-based beverages receive monoamine oxidase (MAO) inhibition ratings for each form of MAO, A+B, which are expressed as percent inhibition relative to a control with no inhibitor present. Examples of ratings for mescal, tequila, Bacanora, sotol and pulque are shown in Example 6. Example 7 shows similar results when the fractions obtained by reverse osmosis are analyzed.

As shown herein, the various agave-derived beverages can be analyzed directly for their contents of MAO A and MAO B inhibitors. This makes possible a rating system wherein the results for a particular beverage could be included on the label. The various beverages could be ranked on a scale based on their contents in comparison to other brands of the same beverage, for example. The ratings could be for combinations of inhibitors for both MAO A and MAO B or for each individually. Thus for a scale of 1-10, with 10 the best rating and 1 the worst, a beverage which shows 80% inhibition of MAO A compared to 40% inhibition shown by a rival brand in the same assays, could be given an 9 vs. 5 for the lower activity beverage. The correlation of inhibition with a particular scale can be designed to provide helpful information to the consumer. The scale used or rating selected need not, of course, be 1-10, but any other scale that might be arbitrarily selected, such as A-F.

The MAO assays used for measuring percent inhibition accept samples with high concentrations of ethanol. The assay method of the invention is necessary to accurately measure inhibition of MAO activity and must tolerate samples with greater than 40% ethanol, which is the main component of the samples of interest to be graded. The range of alcohol typically encountered with distilled agave spirits is 6% for pulque to about 60% for some tequilas and mescal, but more commonly encountered samples will have 40% alcohol (80 proof). Due to the volatility of some (but not all) of the MAO inhibitors derived from agave-based beverages, it is particularly important not to evaporate ethanol from the sample under reduced pressure or by distillation at atmospheric pressure.

The compositions of the invention may be used as a food supplement and/or included in foods or medicines, or used to treat depression, Parkinson's disease or general malaise. The composition may also be used as an adjunct or substitute for coffee or in decaffeinated products. The compositions may be mixed with two or more carriers, excipients and/or diluents that are pharmaceutically or nutritionally acceptable. Thus, in general, the compositions of the invention may be included in juices or other soft drinks such as colas or fruit flavored sodas, or can be consumed directly. The compositions may also be included in foodstuffs such as uncooked liquids, for example salad dressings, and consumed along with the solid components of the salad. The amounts of compositions to be consumed or administered to subjects is highly dependent on the nature of the condition to be treated as well as the concentrations of the MAO inhibitors determined to be in the composition itself. Levels of MAO inhibitors useful for various medical indications are known in the art and these guidelines can be followed. For use as food supplements, this is a matter of the judgment of the nutritionist or other practitioner.

Thus, the invention includes foodstuffs and drinks that contain the composition of the invention in amounts effective to have the desired physiological effect.

One successful method to remove the ethanol from the beverage starting material is reverse osmosis (RO). An RO membrane with a molecular weight cut-off of ~100 Daltons separates ethanol from the inhibitors of MAO's formed by microorganisms or during distillation or inhibitors that may be naturally occurring in the starting material. Isolation of the MAO inhibitors is accomplished without the use of vacuum or distillation. Therefore the invention compositions may be prepared for example, by diluting with distilled water 0.75 liters of tequila (or other distilled agave beverage) to a volume of 7.5-75 liters, depending on the final desired ethanol concentration. For example, 0.75 liters of tequila at 80 proof (40% alcohol by volume) is diluted to 7.5 liters at which point the diluted material is 4% alcohol by volume. The diluted tequila is circulated in a reverse osmosis unit fitted with a membrane with molecular weight cut-off of ~100 Daltons (Tangent Membranes, Inc., RO MINI) wherein the diluted material is concentrated back to a volume of 0.75 liters. Additional reduction of ethanol is achieved by diluting the material again to 7.5 liters or greater and continuing the circulation through the RO unit. For creation of the composition such as an energy drink according to the invention, dilution and subsequent circulation may be continued until the product is considered nonalcoholic. The active MAO inhibitors are then contained in the concentrated, non-alcoholic portion and may then be supplemented with vitamins, minerals, amino acids, protein or caffeine, where desired, and may be included in other food or drink preparations as noted above.

It is an important aspect in the creation of the compositions of the invention that some of the MAO inhibitors are volatile compounds and if the composition is created by evaporation of the ethanol through heated distillation or under reduced pressure, for example, loss of essential MAO inhibitors occurs.

The following examples are offered to illustrate but not to limit the invention.

Example 1

Assay of Various Tequilas Using Commercially Available Assays

A commercial MAO activity kit was employed to test samples of different commercially available tequilas or mezcal, S1, S1 DW, S2 and S3. The kit was purchased from Sigma-Aldrich (Cat. No. MAK136 Monoamine oxidase activity kit) which includes known MAO inhibitor compounds, clorgyline and pargyline, as controls and tyramine as the enzyme substrate. Horseradish peroxidase is also included in this kit to interact with hydrogen peroxide generated from the oxidation of tyramine in order to react with the included label, Amplex® red. The action of MAO A and/or B creates a cascade of events resulting in the fluorescence emission. S1 and S3 are tequilas with S1 an aged version of S3 and S1 DW a distilled water reconstituted sample of S1 after drying under a stream of argon. S2 is a sample of mezcal, which is made from versions of agave other than blue agave. DW is distilled water Fluorescence data are calculated for percent inhibition relative to a buffer control (no inhibitor). A known inhibitor of MAO A, clorgyline, and a known inhibitor of MAO B, pargyline, are included as controls. As shown in FIG. 1, depending upon the sample selective inhibition of MAO A or B may be achieved.

Example 2

Testing Various Tequilas Using a Kynuramine Only Assay

A different assay where kynuramine only is the substrate and assay label is used in this example. This assay uses kynuramine as the MAO substrate and it is a substrate for both MAO A and B. Thus is a more desirable method because effects on peroxidase or spectral interference are eliminated. Kynuramine oxidation results in an OD change at 360 nm and 320 nm. The product is also fluorescent and may be detected by an increase in emission intensity at 400 run with an excitation wavelength at 320 nm.

The assay was set up in clear polystyrene 96-well plates according to the following protocol: Phosphate buffer (205 µl/100 mM/pH 7.2) was added to the wells followed by 20 µl of each extract sample and control inhibitor clorgyline (for MAO A) and pargyline (for MAO B) at 10 µM.

Recombinant human MAO A and MAO B (0.5 mg/ml protein) was purchased from Corning® and each assay was supplied with 3 µg of this protein. Some assays were run with a null protein as a control also supplied by Corning®. The inhibitor(s), buffer and proteins were allowed to pre-incubate in a PowerWave™ optical density reading plate reader set at 37° C. for 10 minutes. The kynuramine substrate was then added to each well and the plate was further incubated at 37° C. for 30 minutes. The plate was read at OD360 nm and the change in absorbance from time zero to 30 minutes was calculated and transformed to % inhibition. Samples S40, S41, S42 are blanco, reposado and añejo, respectively, and are tequilas from the same manufacturer at 0, 1 and 2 stages of aging. 51, S3 are tequilas as in Example 1 and S2 is mezcal. Percent inhibition is calculated from the optical density change at 360 nm from time 0 to 30 min.

Figure 2:
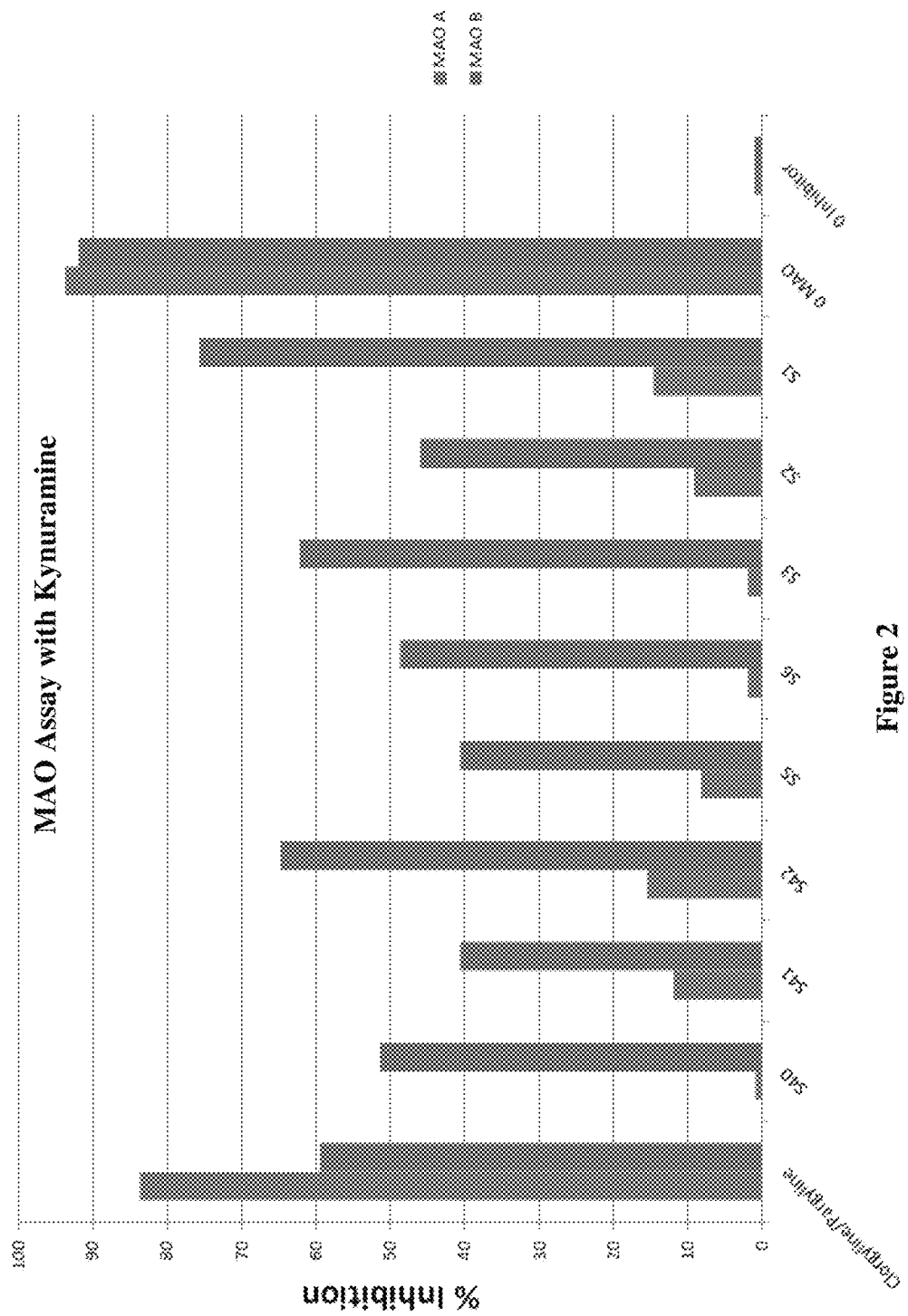
FIG. 2 shows the results of assessing the MAO inhibition activity of various brands and ages of tequila using kynuramine as a substrate.

The results are shown in FIG. 2.

(One tequila used as a sample (DJ1942) containing 40% ethanol was tested for interfering effects on the assay without the alcohol dehydrogenase and NAD and interference was shown.)

Example 3

Effect of Aging

Figure 3:
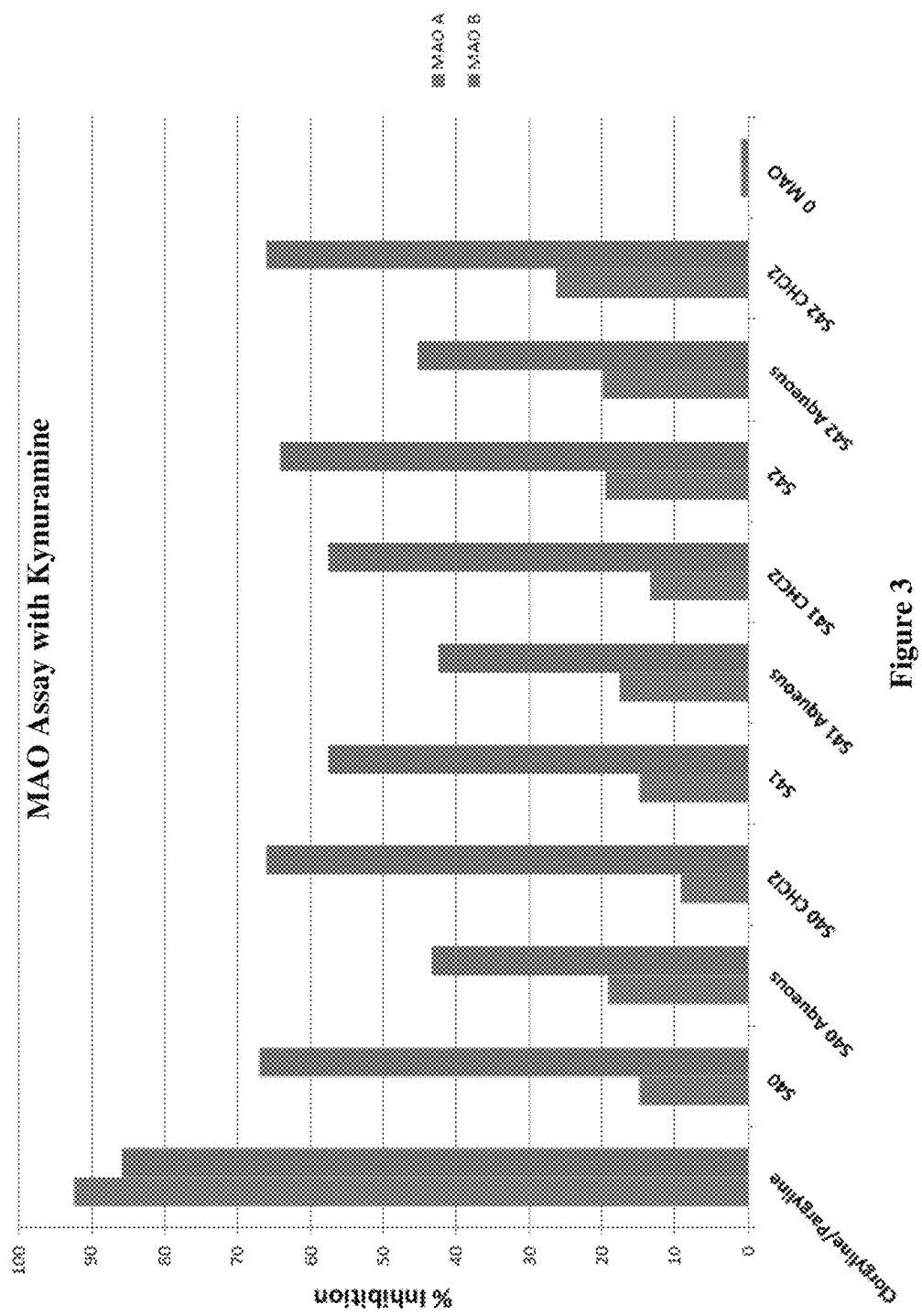
FIG. 3 shows the results of an MAO inhibition assay with kynuramine as a substrate after separation of tequilas into various fractions.

The kynuramine assay was used to test three different ages of tequila, S40, S41, S42 and to compare aqueous and methylene chloride extractions of these samples. The aged tequilas show increased MAO inhibitory activity vs. the younger distillates, as shown in FIG. 3.

Example 4

Fractionation of MAO Inhibitor Activity

Tequila (1750 ml) was diluted to 5000 ml with deionized water and separated into three portions, and each portion was extracted with dichloromethane (4×100 ml). The extracts were combined, washed with deionized water (2×100 ml) and dried over anhydrous sodium sulfate. The sample was reduced in volume to 10 ml by evaporation of solvent using a rotary evaporator then dry silica was added and the solvent was removed at room temperature. The sample-adsorbed silica was dry loaded on a silica column with a 50 ml bed volume and the column was run with a step gradient using hexane:ethyl acetate (100% hexane, 90:10, 80:20, 70:30, 60:40, 50:50, 40:60, 30:70, 20:80, 10:90, 100% ethyl acetate). During the column run 7 ml fractions were collected. The samples were assayed as follows:

The MAO assays for A and B are set up in black Thermo Scientific™ 96-well plates (#7205) with each assay containing 1 µl of sample dissolved in DMSO, 87 µl of 100 mM potassium phosphate buffer pH 7.4, 3 µl of a stock solution of 0.75 mM kynuramine. A set of controls with DMSO alone (0 inhibitor), 1 µl of 50 µmolar clorgyline in DMSO as a MAO A inhibition control and 1 µl of 50 µmolar pargyline in DMSO as a MAO B inhibition control were added on each plate. When optimizing the assays, a no-protein set was sometimes included on the plates.

Recombinant human MAO A and MAO B (Corning®, SUPERSOMES™) was added to the wells for each respective assay at 750 ng protein in 9 µl buffer.

The plate was incubated at 37° C. for 30 minutes and then 100 µl of 2N NaOH was added to each well. The plate was read in a fluorescence spectrophotometer at excitation wavelength 310 and emission wavelength 405.

Figure 4:
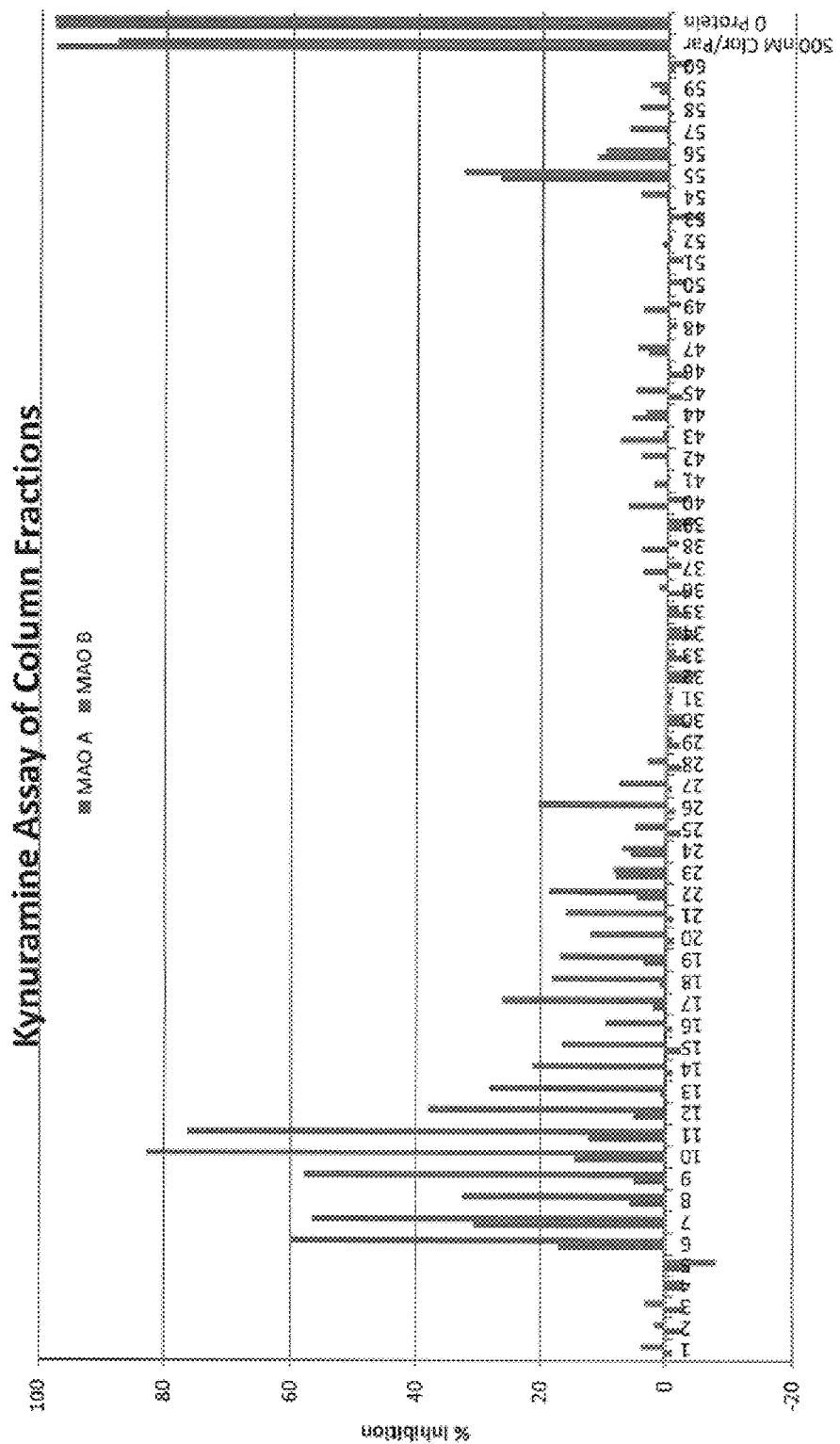
FIG. 4 is a graph showing the MAO inhibition activity of various column fractions based on the kynuramine assay.

To identify inhibitory activity in column fractions 25 µl of each fraction was placed in 1.5 ml microfuge tubes and evaporated to dryness in a Savant™ SpeedVac™ DMSO (5 µl) was added to each tube and 1 µl was assayed for MAO A and B inhibitory activity according to the method above. FIG. 4 shows MAO A and B inhibitory activity across the fractions collected.

Significant MAO inhibition is seen in fractions 6 through 13.

Example 5

Preparation of MAO Inhibitor-Containing Oils

Tequila (100 ml) was diluted to 200 ml with deionized water and extracted with dichloromethane (3×50 ml). The extracts were combined and passed over a column of anhydrous sodium sulfate. The solvent was evaporated using a rotary evaporator and 30 mg of oil was obtained. Samples of this oil inhibited MAO A by 75% and MAO B by 87%.

Tequila (100 ml) was diluted to 200 ml with deionized water and extracted with dichloromethane (3×50 ml). The extracts were combined and passed over a column of anhydrous sodium sulfate. The solvent was removed by evaporation in a Kuderna Danish apparatus warmed over a water bath at 70° C. resulting in 17 mg of an oil. Samples of the oil showed 55% MAO A inhibition and 88% MAO B inhibition.

Example 6

Assay of Various Tequila Samples, Per Se

As discussed above, samples with MAO inhibitory activity must not be evaporated under reduced pressure or the compounds will co-evaporate with ethanol. Therefore, the samples should be assayed without evaporation of ethanol to eliminate losses of MAO inhibiting compounds and in order to accurately grade the MAO inhibitory activity of the product analyzed. The assays were set up in black Thermo Scientific™ 96-well plates (#7205) as follows:

Each assay included 5 µl of sample, 0.975 µg kynuramine dihydrobromide, 0.75 µmoles nicotinamide adenine dinucleotide (NAD) in a total volume of 93 µl with 100 mM phosphate buffered saline, pH 7.4.

Alcohol dehydrogenase was diluted to 0.25 units/ml and 3 µl was added to the wells. The plates were incubated at 25 to 37° C. for 15 minutes.

Human recombinant MAO A and B (Corning) supplied at 5 mg/ml was aliquoted in vials at 20 µl each and diluted for the assay with 246 µl of buffer, then 4 µl of each MAO was added to its respective wells.

The plates were incubated at 37° C. for 30 minutes and 2N NaOH (100 µl) was added and the plates were read at excitation wavelength 310 and emission wavelength 405.

Using this assay, various tequila samples were tested with the results shown in Table 1.

TABLE 1

Ratings of Various Agave-Derived Beverages

| Brand | % Inhibition MAO A | % Inhibition MAO B |
|---|---|---|
| Suerte Blanco | 5 | 6 |
| Suerte Reposado | 7 | 12 |
| Suerte Anejo | 14 | 19 |

TABLE 1-continued

Ratings of Various Agave-Derived Beverages

| Brand | % Inhibition MAO A | % Inhibition MAO B |
|---|---|---|
| Qui blanco | 33 | 7 |
| Don Julio 70th Anniversary | 12 | 6 |
| Grand Patron Piedra | 32 | 49 |
| Don Julio Blanco | 9 | 8 |
| Don Julio Repesado | 18 | 22 |
| Don Julio Anejo | 10 | 26 |
| Don Julio 1942 | 18 | 35 |
| Patron Silver Roca | 39 | 11 |
| Patron Roca Anejo | 21 | 40 |
| Patron Grand Platinum | 38 | 9 |
| Esperanto | 36 | 4 |
| Avion Silver | 31 | 7 |
| 1800 silver | 11 | 11 |
| Cuervo Silver | −1 | 4 |
| Cuervo Gold | 4 | 40 |
| "Cheap" Mezcal | 43 | 2 |
| "Expensive" Mezcal | 40 | 8 |
| Ketel One Vodka | −2 | −2 |
| Jaegermeister | 49 | 55 |
| Tres Generacion | 15 | 41 |
| Clorgyline/Parglyine (positive control) | 97 | 82 |
| DMSO (negative control) | 2 | 1 |
| DMSO (negative control) | −2 | −1 |
| Inhib (positive control) | 98 | 96 |
| Inhib (positive control) | 98 | 95 |

Example 7

Effect of Reverse Osmosis (RO)

An RO Mini from Tangent Membranes, Inc. fitted with a ~100 mwco filter was used to separate the ethanol from tequila while retaining MAO inhibiting compounds. Here, 1.5 liters añejo tequila (DJA) was diluted to 15 liters with distilled water and circulated in the RO Mini until the volume was reduced back to 1.5 liters. The MAO inhibitory activity of 10, 20, 30 and 40 µl of the concentrated sample and the filtrate was assessed. (FIG. 5.)

Figure 5:
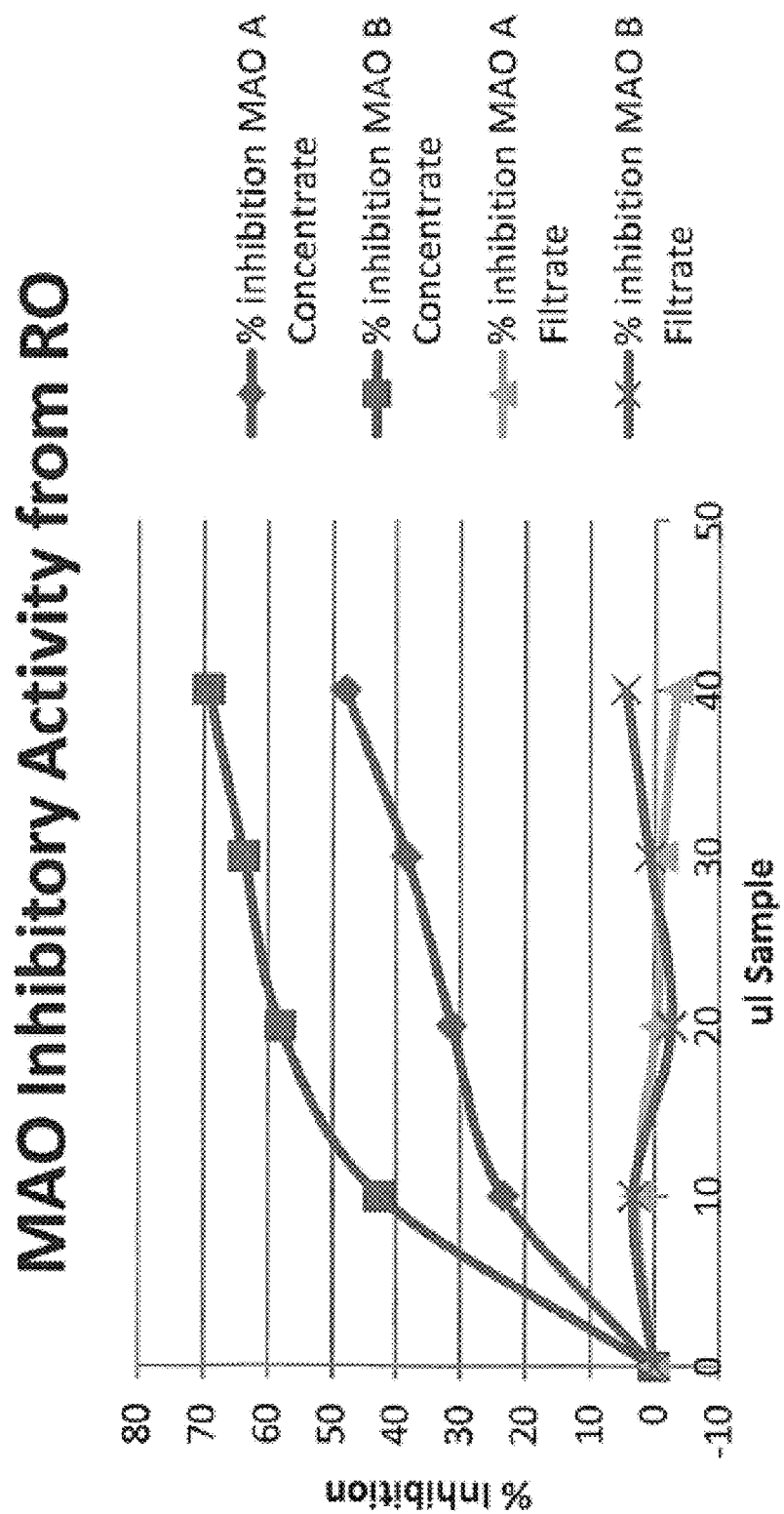
FIG. 5 shows the results of MAO inhibition assays in a sample of tequila that has been subjected to reverse osmosis and compares the activity in the concentrate with the activity in the filtrate.

As shown in FIG. 5, the concentrate retains MAO A and B inhibitors while MAO inhibitors are not present in the filtrate which contains only ethanol and water from the diluted sample.

Table 2 shows the results for various beverages as well as diluted tequila starting material (labeled diluted RO Control), 1st RO Concentrate, 2nd RO Concentrate, 1st RO Filtrate and 2nd RO Filtrate. The filtrates are shown in the MAO inhibition assay to have less inhibitory activity, while most of the activity remains with the concentrate.

TABLE 2

| Sample | MAO A % Inhibition | MAO B % Inhibition |
|---|---|---|
| Kirkland Anejo (Costco brand) | 23 | 32 |
| Milagro Anejo | 26 | 23 |
| Don Julio Anejo | 17 | 32 |
| Don Julio 1942 | 19 | 35 |
| Pulque | 14 | 26 |
| Sotol | 71 | 58 |
| Milagro Barrel Res Anejo | 27 | 15 |
| Diluted RO Control | 17 | 35 |
| 1st RO Concentrate | 23 | 52 |
| 2nd RO Concentrate | 34 | 49 |
| 1st RO Filtrate | 10 | 7 |
| 2nd RO Filtrate | 3 | 8 |
| Clorgyline/Parglyine | 97 | 83 |
| DMSO | 1 | 1 |

The invention claimed is:

1. A composition comprising monoamine oxidase (MAO) inhibitory compounds prepared by removing ethanol from an alcoholic beverage which is a distillate of a fermentation product of an extract of agave by a process that retains volatile compounds other than ethanol.

2. The composition of claim 1 wherein the process is reverse osmosis.

3. The composition of claim 1 wherein the alcoholic beverage is a distillate that has been prepared by:
   a) heating the stems of agave cactus to hydrolyze complex sugars;
   b) shredding and crushing the heated stems to release a syrup;
   c) diluting said syrup with water to a 12-14 BRIX level and inoculating with yeast;
   d) fermenting the inoculated diluted syrup to obtain a fermentation product; and
   e) distilling the fermentation product to obtain the distillate.

4. The composition of claim 3 wherein step a) is conducted by autoclaving.

5. The composition of claim 3 wherein step b) is conducted in a shredding mill and crusher.

6. The composition of claim 3 wherein the process of step d) includes fermentation at between room temperature and 30° C. in the presence of S. cerevisiae and K. africana.

7. The composition of claim 3 wherein step e) is conducted until the distillate reaches an ethanol concentration of at least 38-40% v/v.

8. A foodstuff or drink that comprises the composition of claim 1.

9. A method to treat conditions characterized by overactivity of monoamine oxidase (MAO) which method comprises administering to a subject in need of such treatment an effective amount of the composition of claim 1.

10. The method of claim 9 wherein said condition is depression or Parkinson's disease.

11. A method to treat conditions characterized by overactivity of monoamine oxidase (MAO) which method comprises administering to a subject in need of such treatment an effective amount of the foodstuff or drink of claim 8.

\* \* \* \* \*